United States Patent
Bradley et al.

(10) Patent No.: US 9,463,321 B2
(45) Date of Patent: Oct. 11, 2016

(54) SYSTEM AND METHOD FOR ADJUSTING AUTOMATIC PULSE PARAMETERS TO SELECTIVELY ACTIVATE NERVE FIBERS

(75) Inventors: Kerry Bradley, Glendale, CA (US); Bradley Hershey, Carrolton, TX (US); Dongchul Lee, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1842 days.

(21) Appl. No.: 12/606,050

(22) Filed: Oct. 26, 2009

(65) Prior Publication Data

US 2010/0125314 A1  May 20, 2010

Related U.S. Application Data

(60) Provisional application No. 61/114,951, filed on Nov. 14, 2008.

(51) Int. Cl.
  *A61N 1/08* (2006.01)
  *A61N 1/36* (2006.01)
  *A61N 1/372* (2006.01)

(52) U.S. Cl.
  CPC ....... *A61N 1/36071* (2013.01); *A61N 1/37247* (2013.01)

(58) Field of Classification Search
  USPC ........... 607/1–2, 59–61, 72, 115–118
  See application file for complete search history.

(56) References Cited

U.S. PATENT DOCUMENTS

| | | | |
|---|---|---|---|
| 4,759,368 A * | 7/1988 | Spanton et al. | 607/46 |
| 6,393,325 B1 | 5/2002 | Mann et al. | |
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 7,174,215 B2 | 2/2007 | Bradley | |
| 7,359,751 B1 * | 4/2008 | Erickson et al. | 607/27 |
| 7,539,538 B2 | 5/2009 | Parramon et al. | |
| 2003/0139781 A1 | 7/2003 | Bradley et al. | |
| 2005/0267546 A1 | 12/2005 | Parramon et al. | |
| 2009/0024189 A1 | 1/2009 | Lee et al. | |
| 2010/0010566 A1 | 1/2010 | Thacker et al. | |

OTHER PUBLICATIONS

U.S. Appl. No. 60/951,177, Use of Stimulation Pulse Shape to Control Neural Recruitment Order and Clinical Effect, Inventor: Donghul Lee, et al., filed Jul. 20, 2007.

OTHER PUBLICATIONS

U.S. Appl. No. 61/080,187, System and Method for Converting Tissue Stimulation Programs in a Format Usable by an Electrical Current Steering Navigator, Inventor: James R. Thacker et al., filed Jul. 11, 2008.

Gorman, Peter et al., The Effect of Stimulus Parameters on the Recruitment Characteristics of Direct Nerve Stimulation, IEEE Transactions on Biomedical Engineering, vol. BME-30, No. 7, Jul. 1993, pp. 407-414.

* cited by examiner

*Primary Examiner* — Deborah Malamud

(74) *Attorney, Agent, or Firm* — Schwegman Lundberg & Woessner, P.A.

(57) ABSTRACT

A method of stimulating nerve tissue, a tissue stimulation system, and an external control device are provided. The method, system, and control device cause an electrical stimulus to be applied to at least one electrode adjacent the nerve tissue of a patient. The applied electrical stimulus comprises a plurality of pulses defined by a pulse width value and an amplitude value. The pulse amplitude value is increased (e.g., manually), and the pulse width value is automatically decreased in response to increasing the pulse amplitude value in a manner that increases the intensity of the applied electrical stimulus. Alternatively, the pulse width value may be decreased (e.g., manually), and the pulse amplitude value automatically increased in response to decreasing the pulse width value in a manner that increases the intensity of the applied electrical stimulus.

10 Claims, 8 Drawing Sheets

SYSTEM AND METHOD FOR ADJUSTING AUTOMATIC PULSE PARAMETERS TO SELECTIVELY ACTIVATE NERVE FIBERS

RELATED APPLICATION

The present application claims the benefit under 35 U.S.C. §119 to U.S. provisional patent application Ser. No. 61/114,951, filed Nov. 14, 2008. The foregoing application is hereby incorporated by reference into the present application in its entirety.

FIELD OF THE INVENTION

The present invention relates to tissue stimulation systems, and more particularly, to a system and method for stimulating nerve fibers.

BACKGROUND OF THE INVENTION

Implantable neurostimulation systems have proven therapeutic in a wide variety of diseases and disorders. Spinal Cord Stimulation (SCS) techniques, which directly stimulate the spinal cord tissue of the patient, have long been accepted as a therapeutic modality for the treatment of chronic pain syndromes, and the application of spinal cord stimulation has begun to expand to additional applications such as angina pectoralis and incontinence. In recent investigations, Peripheral Stimulation (PS), which includes Peripheral Nerve Field Stimulation (PNFS) techniques that stimulate nerve tissue directly at the symptomatic site of the disease or disorder (e.g., at the source of pain), and Peripheral Nerve Stimulation (PNS) techniques that directly stimulate bundles of peripheral nerves that may not necessarily be at the symptomatic site of the disease or disorder, has demonstrated efficacy in the treatment of chronic pain syndromes and incontinence, and a number of additional applications are currently under investigation.

These implantable neurostimulation systems typically include one or more electrode carrying stimulation leads, which are implanted at the desired stimulation site, and a neurostimulator implanted remotely from the stimulation site, but coupled either directly to the stimulation lead(s) or indirectly to the stimulation lead(s) via a lead extension. Thus, electrical pulses can be delivered from the neurostimulator to the stimulation electrode(s) to stimulate or activate a volume of tissue, thereby providing the desired efficacious therapy to the patient.

The neurostimulation system may further comprise a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer (CP), which typically includes a general purpose computer, such as a laptop, with a programming software package installed thereon.

Individual electrode contacts (the "electrodes") are arranged in a desired pattern and spacing in order to create an electrode array. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include electrical pulse parameters, which may define the pulse amplitude (measured in milliamps or volts depending on whether constant current or constant voltage is supplied to the electrodes), pulse width (measured in microseconds), pulse rate (measured in pulses per second), pulse shape, and burst rate (measured as the stimulation on duration per unit time). Each electrode combination, along with the electrical pulse parameters, can be referred to as a "stimulation parameter set." The best stimulus parameter set will typically be one that delivers stimulation energy to the volume of tissue that must be stimulated in order to provide the therapeutic benefit (e.g., pain relief), while minimizing the volume of non-target tissue that is stimulated.

Typically, the therapeutic effect for any given neurostimulation application may be optimized by adjusting the stimulation parameters. For example, the volume of activated tissue in any given neurostimulation application may be increased or decreased by adjusting certain stimulation parameters, such as amplitude and pulse width. Often, these therapeutic effects are correlated to the diameter of the nerve fibers that innervate the volume of tissue to be stimulated (i.e., for different stimulation applications, different fiber diameters can encode different sensations).

For example, in PNFS and PNS applications, there is often a distribution of fiber diameters near the electrodes that strongly encode different sensations. For example, the larger Abeta afferent nerve fibers in the periphery can encode vibration and pressure, whereas the smaller Adelta nerve fibers often encode sharp pain. In these applications, if the stimulation amplitude is increased for a fixed electrode combination and pulse width, the activation of the large nerve fibers will be increased prior to the activation of the small nerve fibers due to the inherent nature of fiber diameters and the electrical field external to the nerve fibers. However, the patient may reach an amplitude limit due to the activation of the smaller nerve fibers that generate side effects before the larger nerve fibers that provide the intended therapy. Thus, stimulation of the small diameter nerve fibers may lead to other uncomfortable, painful sensations near the stimulating electrode, thereby producing side effects and limiting therapeutic coverage. Therefore, in certain stimulation applications, control of nerve fiber recruitment based on diameter might be critically important to maximize the therapeutic effect of the stimulation.

In contrast, in SCS applications, activation of different nerve fiber diameters does not necessarily encode different sensations or side effects. In particular, in SCS, activation (i.e., recruitment) of large diameter sensory fibers in the dorsal column of the spinal cord creates a sensation known as paresthesia that can be characterized as an alternative sensation that replaces the pain signals sensed within the affected region of the patient's body. Thus, it has been believed that the large diameter nerve fibers are the major targets for SCS. However, the distribution of sensory nerve fiber diameters in the dorsal column is an artifact of where the fibers enter the spinal cord and the specific spinal cord segment stimulated. Since the nerve fibers in the dorsal column tend to be mostly sensory nerve fibers, it is generally believed that different fiber diameter activation merely would result in more or less paresthesia in different parts of the patient's body—essentially all innocuous, if not therapeutic stimulation. Therefore, in some stimulation applications, control of nerve fiber recruitment based on diameter might not be as critically important to maximize the therapeutic effect of the stimulation.

Thus, there remains a need to selectively provide a means for stimulating a specific range of nerve fiber diameters over a range of different stimulation amplitude levels.

SUMMARY OF THE INVENTION

In accordance with a first aspect of the present inventions, a method of stimulating nerve tissue (e.g., peripheral nerve tissue) is provided. The method comprises applying an electrical stimulus to at least one electrode adjacent the nerve tissue of a patient (e.g., during a fitting procedure). The applied electrical stimulus comprises a plurality of pulses defined by a pulse width value and an amplitude value. The method may optionally comprise implanting the electrode(s) adjacent the nerve tissue.

The method further comprises increasing the pulse amplitude value (e.g., manually), and automatically decreasing the pulse width value in response to increasing the pulse amplitude value in a manner that increases the intensity of the applied electrical stimulus. Alternatively, the method may comprise increasing the pulse width value (e.g., manually), and automatically decreasing the pulse amplitude value in response to increasing the pulse width value in a manner that increases the intensity of the applied electrical stimulus. As one example, the pulse amplitude value and/or pulse width value can be increased in a manner that stimulates nerve fibers of a smaller diameter, but prevents stimulation of Adelta nerve fibers adjacent the at least one electrode. The pulse amplitude value and/or pulse width value may be adjusted, e.g., by using an external control device.

In accordance with a second aspect of the present inventions, a tissue stimulation system is provided. The system comprises a pulse generating device (e.g., an implantable pulse generator) for generating an electrical stimulus having a plurality of pulses defined by a pulse width value and an amplitude value, and at least one electrode for delivering the electrical stimulus to adjacent nerve tissue. The system further comprises a user interface device configured for allowing a user to prompt an increase in the pulse amplitude value or prompt a decrease in the pulse width value (which may be accomplished manually), and an external control device configured for automatically decreasing the pulse width value in response to increasing the pulse amplitude value or automatically increasing the pulse amplitude value in response to decreasing the pulse width value in a manner that increases the intensity of the electrical stimulus.

In accordance with a third aspect of the present inventions, an external control device for a neurostimulation device is provided. The external control device comprises a user interface capable of receiving an input (e.g., a manual input) from a user. The external control device further comprises a processor configured for varying an amplitude value and a pulse width value of an electrical stimulus generated by a pulse generating device by increasing the pulse amplitude value while decreasing the pulse width value or decreasing the pulse width value while increasing the pulse amplitude value in response to the user input in a manner that increases the intensity of the applied electrical stimulus. The processor is further configured generating a stimulation parameter set from the varied amplitude value and pulse width value. The pulse generating device may be programmed with the stimulation parameter set. The external control device further comprises output circuitry configured for transmitting the stimulation parameter set to the pulse generating device.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
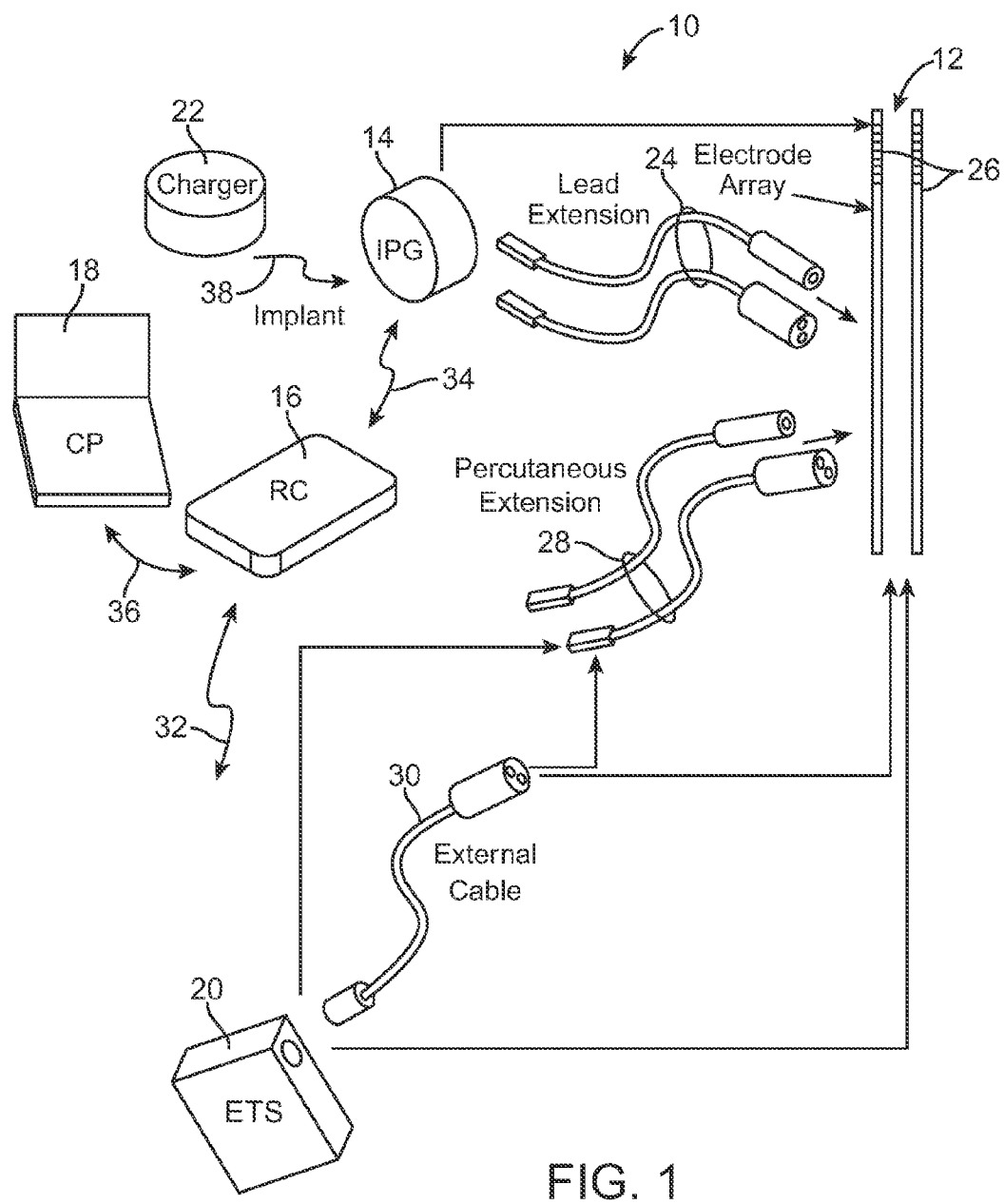
FIG. 1 is perspective view of one embodiment of a tissue stimulation system arranged in accordance with the present inventions.

Turning first to FIG. 1, an exemplary nerve tissue stimulation system 10 generally includes one or more (in this case, two) implantable stimulation leads 12, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail-below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). For purposes of brevity and clarity, only the IPG 14 will be referred to hereafter. The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
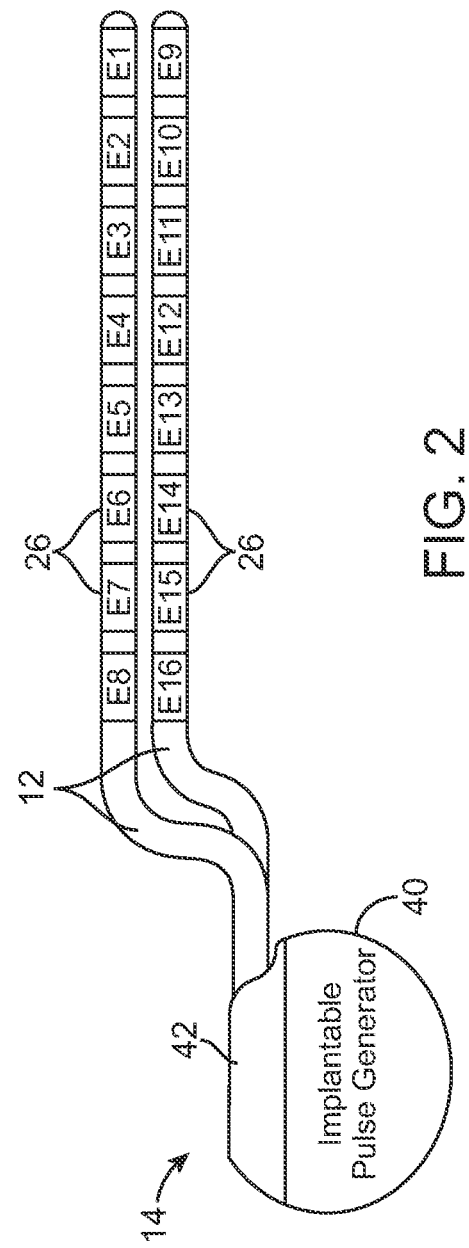
FIG. 2 is a side view of an implantable pulse generator and a pair of stimulation leads that can be used in the tissue stimulation system of FIG. 1.

Referring now to FIG. 2, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mate in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As briefly discussed above, the IPG 14 includes battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 3:
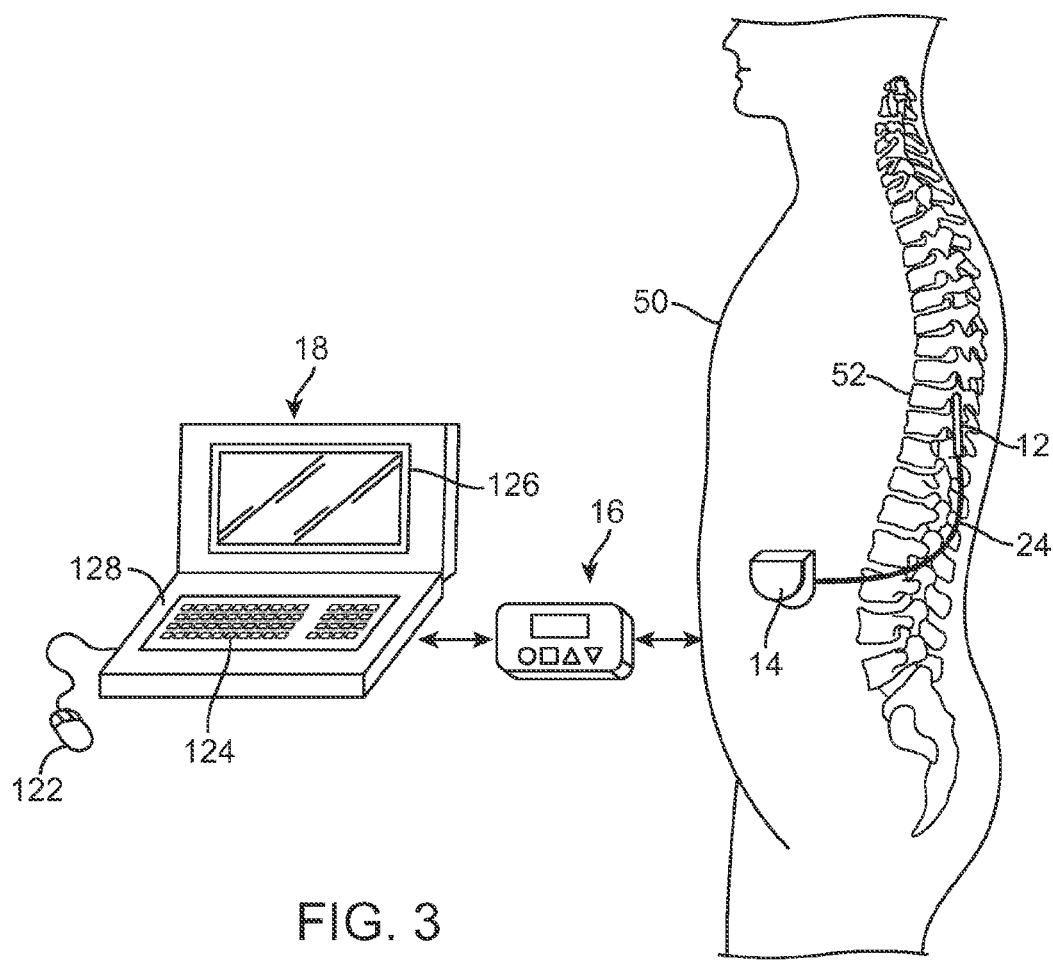
FIG. 3 is a plan view of the tissue stimulation system of FIG. 1 in use with a patient.

For spinal cord stimulation (SCS) applications, the electrode leads 12 are implanted within the spinal column 52 of a patient 50, as shown in FIG. 3. For spinal cord stimulation (SCS) applications, the preferred placement of the electrode leads 12 is adjacent, i.e., resting near, or upon the dura, adjacent to the spinal cord area to be stimulated. For peripheral stimulation (PS) applications, the electrode leads 12 are implanted remotely from the spinal cord; for example, subcutaneously in the lower back (not shown in FIG. 3) or any other region where peripheral nerves can be stimulated. For the purposes of this specification, peripheral nerve tissue is any nerve tissue that is not part of the central nervous system (i.e., nerve tissue other than the brain or spinal cord). The IPG 14 is generally implanted in a surgically-made pocket either in the abdomen or above the buttocks. The IPG 14 may, of course, also be implanted in other locations of the patient's body. The lead extension 24 facilitates locating the IPG 14 away from the electrode leads 12. As there shown, the CP 18 communicates with the IPG 14 via the RC 16.

Figure 4:
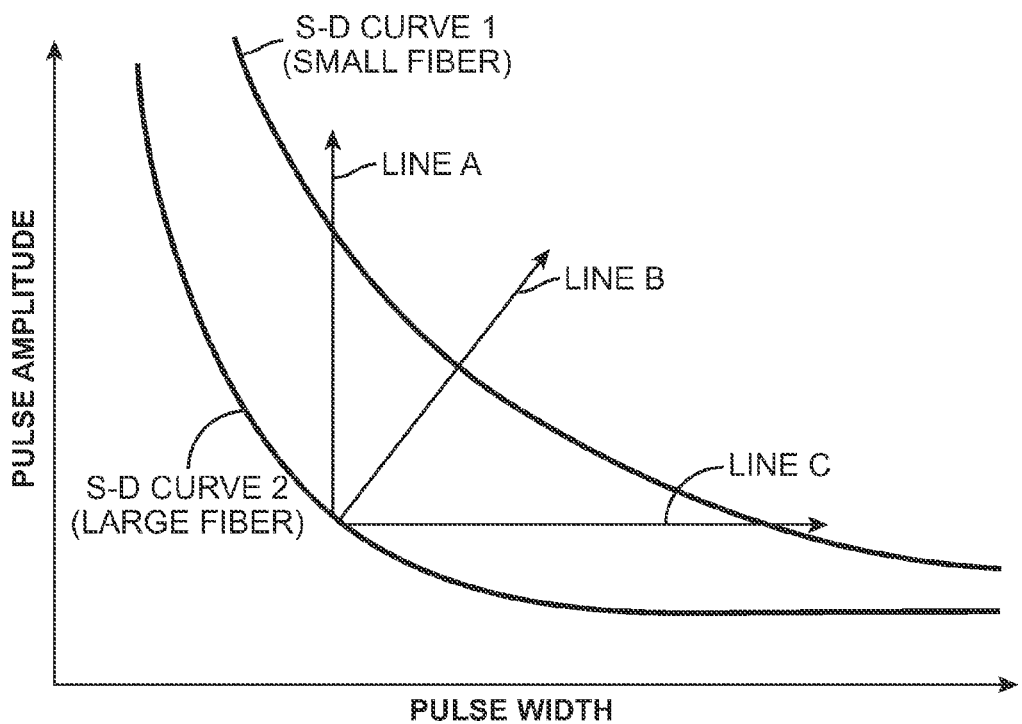
FIG. 4 is an exemplary plot of two strength-duration curves for respective small diameter fibers and large diameter fibers and the variance of a pulse amplitude and pulse width of stimulation energy relative to the curves when the system is in a Spinal Cord Stimulation (SCS) mode.
Figure 5:
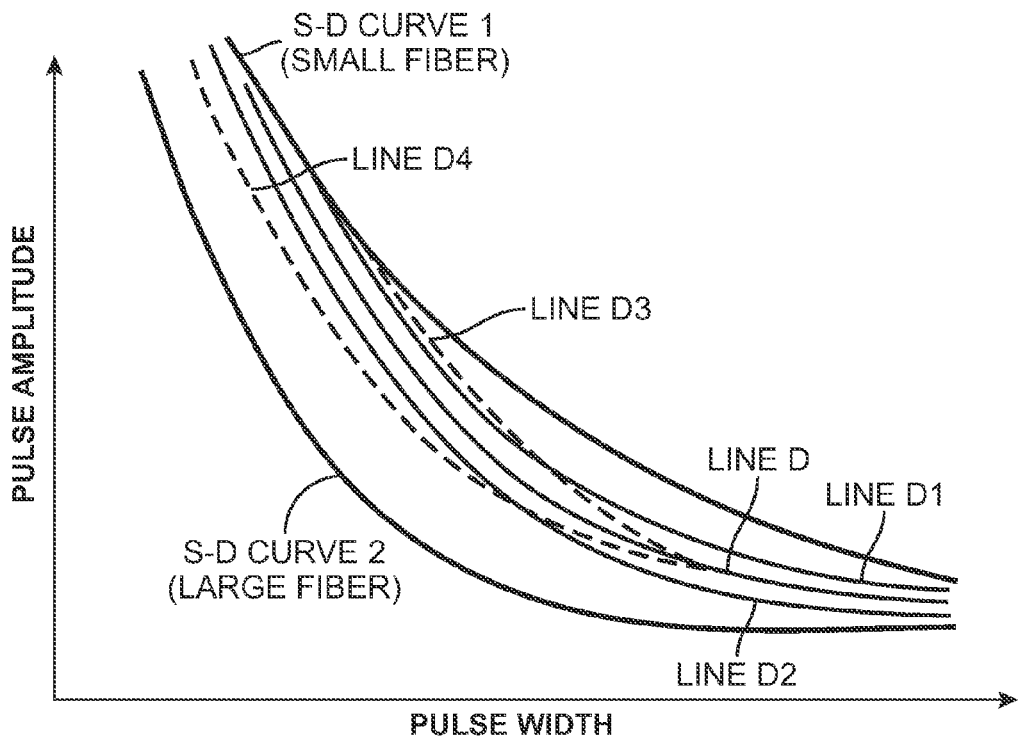
FIG. 5 is an exemplary plot of two strength-duration curves for respective small diameter fibers and large diameter fibers and the variance of a pulse amplitude and pulse width of stimulation energy relative to the curves when the system is in a Peripheral Stimulation (PS) mode.

Significant to the present inventions, the tissue stimulation system 10 can be selectively operated between a spinal cord stimulation (SCS) mode (FIG. 4) and a peripheral stimulation (PS) mode (FIG. 5). In both modes, the intensity of the electrical energy conveyed through the target nerve tissue can be increased by adjusting the pulse amplitude and/or pulse width of the electrical energy relative to strength-duration curves, which represent the pulse amplitude and pulse width needed to stimulate nerve fibers of specified diameters. As shown in FIGS. 4 and 5, S-D curve 1 represents the strength-duration curve for a relatively small nerve fiber, whereas S-D curve 2 represents the strength-duration curve for a relatively large nerve fiber.

In the SCS mode, the system 10 increases the intensity of electrical energy relatively quickly, thereby stimulating nerves of decreasingly smaller diameters relatively quickly. Because the nerve fibers in the dorsal column tend to be mostly sensory nerve fibers, the activation of different fiber diameters is essentially innocuous, and therefore, it may be advantageous to recruit as many nerve fibers—albeit with different diameters, as possible to provide for a more efficient programming process.

In the illustrated embodiment, the system 10, when in the SCS mode, allows a user to manually increase the pulse amplitude of the electrical energy or automatically increases the pulse amplitude of the electrical energy without modifying the pulse width the electrical energy, as shown by Line A in FIG. 4. Alternatively, the system 10 allows a user to manually increase the pulse amplitude of the electrical energy while automatically increasing the pulse width of the electrical energy, allows a user to manually increase the pulse width of the electrical energy while automatically increasing the pulse amplitude of the electrical energy, or automatically increases both the pulse amplitude and pulse width of the electrical energy, as shown by Line B. Further details discussing techniques for increasing both the pulse amplitude and pulse width of electrical energy are provided in U.S. Pat. No. 7,174,215, which is expressly incorporated herein by reference. Alternatively, the system 10 allows a user to manually increase the pulse width of the electrical energy or automatically increases the pulse width of the electrical energy without modifying the pulse amplitude of the electrical energy, as shown by Line C.

In the PS mode, the system 10 increases the intensity of electrical energy relatively gradually, thereby stimulating nerves of decreasingly smaller diameters gradually, relative to more distal, larger diameter nerves. Because the peripheral nerves typically include smaller Adelta nerve fibers that encode sharp pain, it is desirable that the intensity of the electrical energy be increased gradually.

In the illustrated embodiment, the system 10, when in the PS mode, allows a user to increase the intensity of the stimulation. In particular, the system 10 allows the user to manually increase the pulse amplitude of the electrical energy while automatically decreasing the pulse width of the electrical energy, allows a user to manually decrease the pulse width of the electrical energy while automatically increasing the pulse amplitude of the electrical energy, and/or automatically increases the pulse amplitude while automatically decreasing the pulse width of the electrical energy, as shown by Line D in FIG. 5. Although the manual decrease of the pulse width is usually not associated with an increase in stimulation intensity, the accompanying increase the pulse amplitude will effect the increase in the stimulation intensity. Notably, although all three these adjustments increases the intensity of the electrical energy, thereby potentially activating Adelta nerve fibers, the decreasing of the pulse width takes advantage of the increasing threshold difference between smaller and larger nerve fibers with the decreasing pulse width (See P. H. Gorman and J. T. Mortimer, "The effect of stimulus parameters on the recruitment characteristics of direct nerve stimulation," IEEE Trans. Biomed. Eng., vol. 30, pp. 407-414, July 1983). As a result, it may be easier to gradually recruit the smaller innocuous nerve fibers without activating the pain carrying Adelta nerve fibers.

Notably, the offset of the pulse amplitude-pulse width curve D can be adjusted to set the initial nerve diameter that is stimulated by the electrical energy. For example, the offset can be increased, as shown by Line D1, or the offset can be decreased, as shown by Line D2. The shape of the pulse amplitude-pulse width Line D can also be adjusted to increase or decrease the rate at which the intensity of the electrical energy is increased. For example, the rate at which the intensity of the electrical energy is changed can be increased, as shown by Line D3 (shown in phantom), or the rate at which the intensity of the electrical energy is changed can be decreased, as shown by Line D4 (shown in phantom).

Although the pulse amplitude and pulse width of the electrical energy output by the IPG 14 may be controlled by either the RC 16 or the CP 18, the CP 18 is described herein as having the means for adjusting the pulse amplitude and pulse width.

Figure 6:
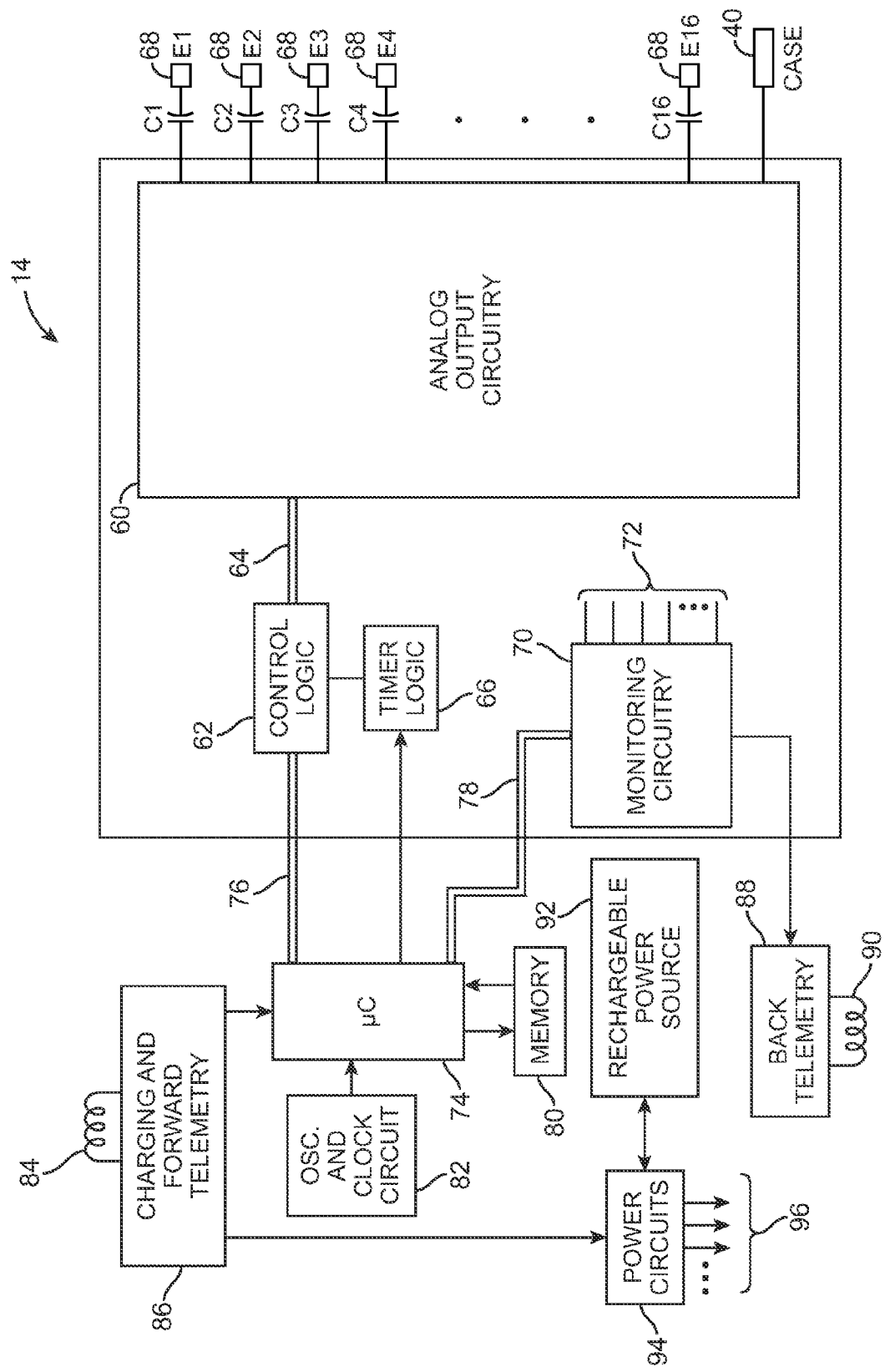
FIG. 6 is a block diagram of the internal componentry of the IPG of FIG. 2.

Turning next to FIG. 6, the main internal components of the IPG 14 will now be described. The IPG 14 includes analog output circuitry 60 configured for generating electrical stimulation energy in accordance with a defined pulsed waveform having a specified pulse amplitude, pulse rate, pulse width, and pulse shape under control of control logic 62 over data bus 64. Control of the pulse rate and pulse width of the electrical waveform is facilitated by timer logic circuitry 66, which may have a suitable resolution, e.g., 10 µs. The stimulation energy generated by the analog output circuitry 60 is output via capacitors C1-C16 to electrical terminals 68 corresponding to electrodes E1-E16.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference. The analog output circuitry 60 may also comprise pulse shaping circuitry (not shown) capable of shaping the pulses (e.g., a square pulse, an exponential pulse, a logarithmic pulse, a ramped pulse, a trapezoidal pulse, etc.). Further details discussing pulse shaping circuitry and the different pulse shapes that can be generated are disclosed in U.S. Patent Application Ser. No. 60/951,177, entitled "Use of Stimulation Pulse Shape to Control Neural Recruitment Order and Clinical Effect," which is expressly incorporated herein by reference.

The IPG 14 further comprises monitoring circuitry 70 for monitoring the status of various nodes or other points 72 throughout the IPG 14, e.g., power supply voltages, temperature, battery voltage, and the like. The monitoring circuitry 70 is also configured for measuring electrical parameter data (e.g., electrode impedance and/or electrode field potential). The IPG 14 further comprises processing circuitry in the form of a microcontroller (μC) 74 that controls the control logic 62 over data bus 76, and obtains status data from the monitoring circuitry 70 via data bus 78. The IPG 14 further comprises memory 80 and oscillator and clock circuit 82 coupled to the μC 74. The μC 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the μC 74 generates the necessary control and status signals, which allow the μC 74 to control the operation of the IPG 14 in accordance with a selected operating program and stimulation parameters. In controlling the operation of the IPG 14, the μC 74 is able to individually generate stimulus pulses at the electrical terminals 68 using the analog output circuitry 60, in combination with the control logic 62 and timer logic circuitry 66, thereby allowing each electrical terminal 68 to be paired or grouped with other electrical terminals 68, including the monopolar case electrode, to control the polarity, amplitude, rate, pulse width, pulse shape, and channel through which the current stimulus pulses are provided. The μC 74 facilitates the storage of electrical parameter data measured by the monitoring circuitry 70 within memory 80.

The IPG 14 further comprises a receiving coil 84 for receiving programming data (e.g., the operating program and/or stimulation parameters) from the external programmer (i.e., the RC 16 or CP 18) in an appropriate modulated carrier signal, and charging, and circuitry 86 for demodulating the carrier signal it receives through the receiving coil 84 to recover the programming data, which programming data is then stored within the memory 80, or within other memory elements (not shown) distributed throughout the IPG 14.

The IPG 14 further comprises back telemetry circuitry 88 and a transmission coil 90 for sending informational data to the external programmer. The back telemetry features of the IPG 14 also allow its status to be checked. For example, when the CP 18 initiates a programming session with the IPG 14, the capacity of the battery is telemetered, so that the CP 18 can calculate the estimated time to recharge. Any changes made to the current stimulus parameters are confirmed through back telemetry, thereby assuring that such changes have been correctly received and implemented within the implant system. Moreover, upon interrogation by the CP 18, all programmable settings stored within the IPG 14 may be uploaded to the CP 18.

The IPG 14 further comprises a rechargeable power source 92 and power circuits 94 for providing the operating power to the IPG 14. The rechargeable power source 92 may, e.g., comprise a lithium-ion or lithium-ion polymer battery or other form of rechargeable power. The rechargeable source 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits) received by the receiving coil 84.

To recharge the power source 92, the external charger 22 (shown in FIG. 1), which generates the AC magnetic field, is placed against, or otherwise adjacent, to the patient's skin over the implanted IPG 14. The AC magnetic field emitted by the external charger induces AC currents in the receiving coil 84. The charging and forward telemetry circuitry 86 rectifies the AC current to produce DC current, which is used to charge the power source 92. While the receiving coil 84 is described as being used for both wirelessly receiving communications (e.g., programming and control data) and charging energy from the external device, it should be appreciated that the receiving coil 84 can be arranged as a dedicated charging coil, while another coil, such as the coil 90, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 7:
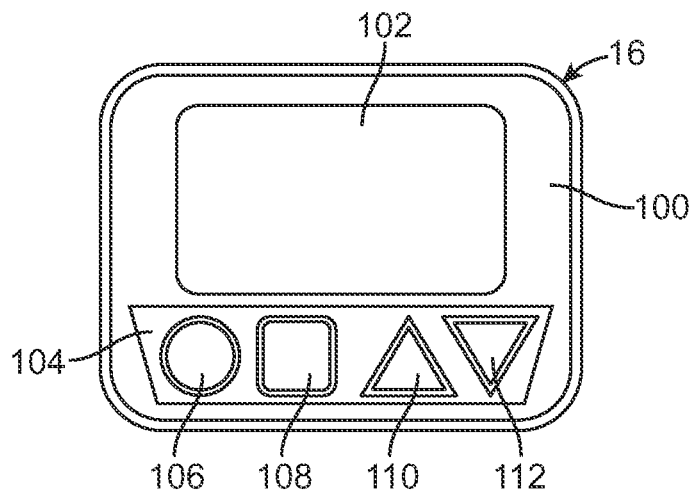
FIG. 7 is a plan view of a remote control that can be used in the system of FIG. 1.

Referring now to FIG. 7, one exemplary embodiment of an RC 16 will now be described. As previously discussed, the RC 16 is capable of communicating with the IPG 14 or CP 18. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touch-screen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 16 to switch between screen displays and/or parameters. The buttons 110 and 112 serve as up/down buttons that can actuated to increment or decrement any of stimulation parameters of the pulse generated by the IPG 14, including pulse amplitude, pulse width, and pulse rate. For example, the selection button 108 can be actuated to place the RC 16 in an "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112.

Optionally, the RC 16 may be placed in a "Pulse Shaping Adjustment Mode," which is described in further detail in U.S. Patent Application Ser. No. 60/951,177, which was previously incorporated herein by reference.

Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 8:
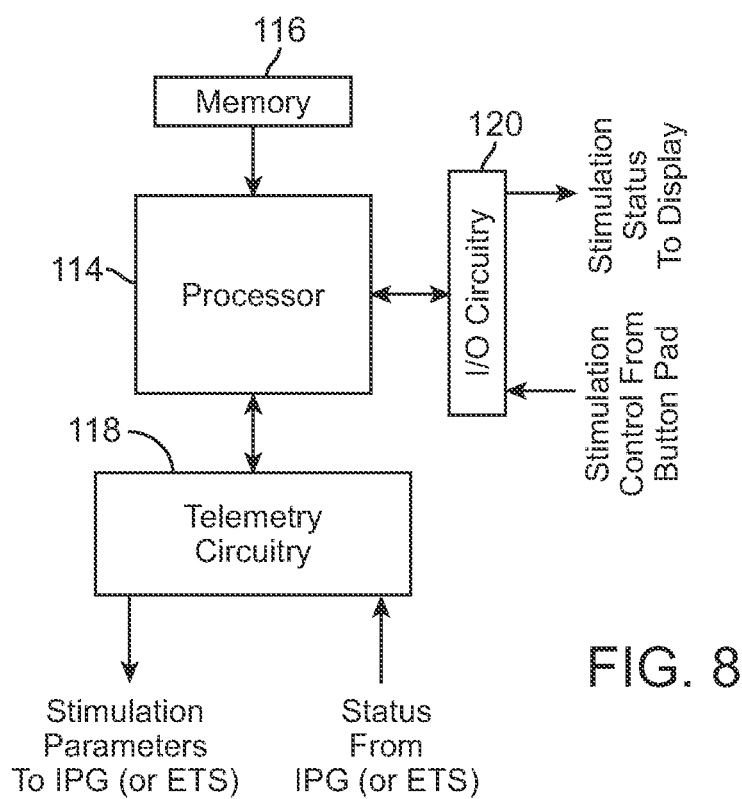
FIG. 8 is a block diagram of the internal componentry of the remote control of FIG. 7.

Referring to FIG. 8, the internal components of an exemplary RC 16 will now be described. The RC 16 generally includes a processor 114 (e.g., a microcontroller), memory 116 that stores an operating program for execution by the processor 114, as well as stimulation parameter sets (which can be generated from a look-up table or a formula), input/output circuitry, and in particular, telemetry circuitry 118 for outputting stimulation parameters to the IPG 14 and receiving status information from the IPG 14, and input/output circuitry 120 for receiving stimulation control signals from the button pad 104 and transmitting status information to the display screen 102 (shown in FIG. 7). As well as controlling other functions of the RC 16, which will not be described herein for purposes of brevity, the processor 114 generates new stimulation parameter sets in response to the user operation of the button pad 104. These new stimulation parameter sets would then be transmitted to the IPG 14 via the telemetry circuitry 118. Further details discussing the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 3, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18, under the control of the clinician, may actively control the characteristics of the electrical stimulation generated by the IPG 14 to allow the optimum stimulation parameters to be determined based on patient feedback and for subsequently programming the IPG 14 with the optimum stimulation parameters.

Figure 9:
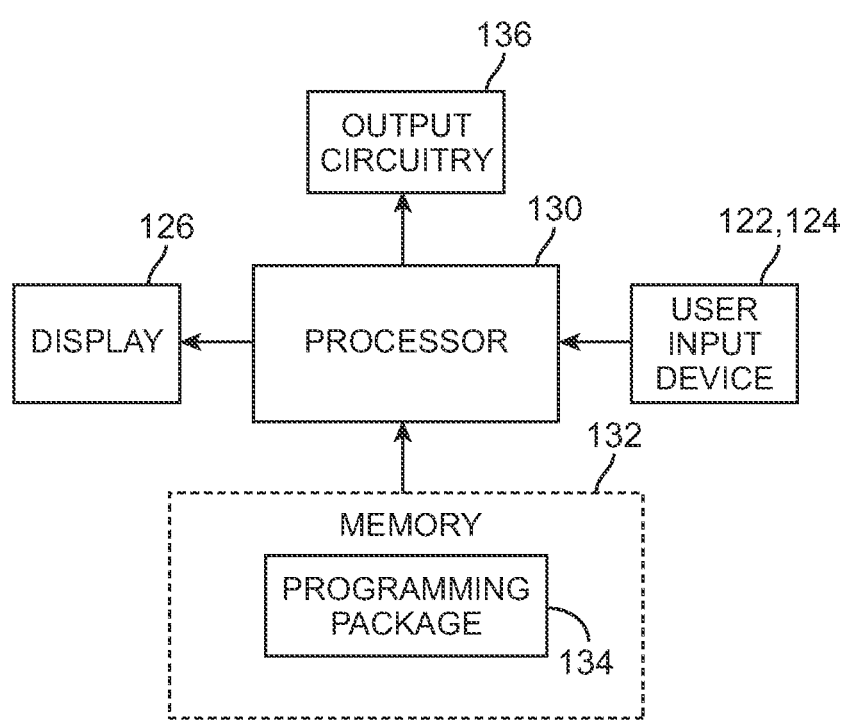
FIG. 9 is a block diagram of the components of a computerized programming system that can be used in the system of FIG. 1.

As shown in FIG. 9, the CP 18 generally includes a processor 130 (e.g., a central processor unit (CPU)) and memory 132 that stores a stimulation programming package 134, which can be executed by the processor 130 to allow a clinician to program the IPG 14 and RC 16. The memory 132 also stores data defining various pulse amplitude-pulse width lines (such as those illustrated in FIGS. 4 and 5). In performing this function, the processor 130 generates a plurality of stimulation parameter sets from the parameter values manually varied by the user via operation of the user input device 122, 124, or otherwise automatically varied by the processor 130 itself. The CP 18 further includes output circuitry 136 (e.g., via the telemetry circuitry of the RC 16) for downloading stimulation parameters to the IPG 14 and RC 16 and for uploading stimulation parameters already stored in the memory 116 of the RC 16, via the telemetry circuitry 118 of the RC 16. To allow the clinician to perform these functions, the CP 18 includes a user input device (e.g., a mouse 122 and keyboard 124 shown in FIG. 3), and a display monitor 126 housed in a case 128 (also shown in FIG. 3).

Further details discussing user interfaces and exemplary stimulation programming packages are described in U.S. Pat. No. 6,393,325 and U.S. Patent Application Ser. No. 61/080,187, entitled "System and Method for Converting Tissue Stimulation Programs in a Format Usable by an Electrical Current Steering Navigator," which are expressly incorporated herein by reference.

Figure 10:
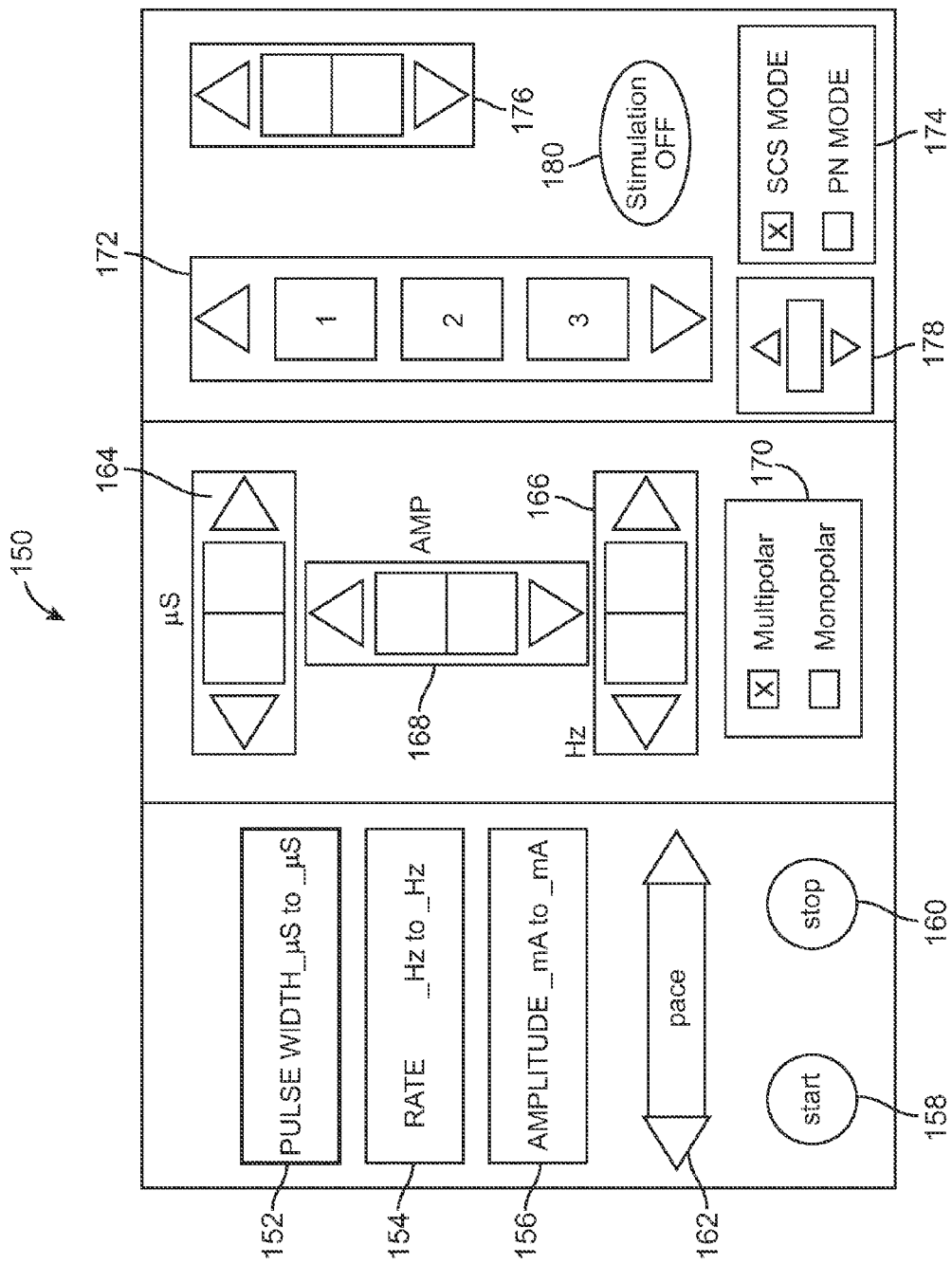
FIG. 10 is view of a programming screen and generated by the computerized programming system of FIG. 9.

An example of a programming screen 150 that can be generated by the CP 18 is shown in FIG. 10. The programming screen 150 allows a user to perform automated stimulation parameter testing, manual stimulation parameter testing, and electrode combination selection functions.

The programming screen 150 includes various stimulation parameter entries that define the ranges of stimulation parameters to be automatically tested. In particular, the programming screen includes a pulse width entry 152 (expressed in microseconds (μs)), a pulse rate entry 154 (expressed in Hertz (Hz)), and a pulse amplitude entry 156 (expressed in milliamperes (mA)). The user may enter a "begin" value and an "end" value for each stimulation parameter to be automatically adjusted. In one embodiment, only a single parameter (e.g., pulse width entry 152) is highlighted to be auto-adjusted. The programming screen 150 also includes a start button 158, which begins the automatic adjustment of the highlighted stimulation parameter from its "begin" value through a minimum increment to its "end" value, and a stop button 160, which halts the automatic adjustment of the highlighted stimulation parameter. The programming screen 150 also includes a pacing control 162, the left arrow of which can be clicked to decrease the speed of the parameter adjustment and the right arrow of which can be clicked to increase the speed of the parameter adjustment.

The programming screen 150 also includes various stimulation parameter controls that can be operated by the user to manually adjust stimulation parameters. In particular, the programming screen 150 includes a pulse width adjustment control 164 (expressed in microseconds (μs)), a pulse rate adjustment control 166 (expressed in Hertz (Hz)), and a pulse amplitude adjustment control 168 (expressed in milliampheres (mA)). Each control includes a first arrow that can be clicked to decrease the value of the respective stimulation parameter and a second arrow that can be clicked to increase the value of the respective stimulation parameter. The programming screen 150 also includes multipolar/monopolar stimulation selection control 170, which includes check boxes that can be alternately clicked by the user to provide multipolar or monopolar stimulation.

The programming screen 150 also includes an electrode combination control 172 having arrows that can be clicked by the user to select one of three different electrode combinations 1-3. Each of the electrode combinations 1-3 can be conventionally created either manually; for example, clicking on selected electrodes of a graphical electrode array (not shown) as anodes and cathodes and defining a percentage anodic current or cathodic current for each selected electrode (e.g., turning off electrode E1 as an anode, and turning on electrode E2 as an anode, and defining an anodic current for electrode E2), or automatically; for example, by gradually shifting current between anodic ones of the electrodes and/or gradually shifting current between cathodic ones of the electrodes via a directional device, such as a joystick or mouse (e.g., shifting anodic electrical current from electrode E1 to electrode E2 in 5% increments).

The programming screen 150 comprises a pulse amplitude-pulse width auto adjust control 174, which includes check boxes that can be alternately clicked by the user to selectively place the system 10 between an SCS mode (no auto adjust) and a PS mode (auto adjust), as described above with respect to FIGS. 4 and 5. Alternatively, as another example, the auto-adjust control 174 may be incorporated into the programming interface device as a button or key that is pressed when activated and then depressed when released, such as an Alt key. Other examples are easily incorporated into a parameter adjustment screen. The programming screen 150 further includes an offset adjustment control 176 having arrows that can be clicked by the user to vary the offset of the pulse amplitude-pulse width line (e.g., Lines D1 and D2 in FIG. 5), and a line shaping adjustment control 178 having arrows that can be clicked by the user to increase or decrease the rate at which the intensity is increased (e.g., Lines D3 and D4 in FIG. 5). The programming screen 150 further comprises a stimulation on/off control 180 that can be alternately clicked to turn the stimulation on or off.

When the system 10 is in the SCS mode by clicking the No Auto Adjust check box in the auto-adjust control 174, the user may click the start button 158, so that the pulse amplitude value and/or pulse width value are automatically increased to quickly increase the intensity of the resulting electrical energy (e.g., such that the pulse amplitude values and/or pulse width values follow one of Lines A-C illustrated in FIG. 4). If both the pulse amplitude value and the pulse width value are to be automatically increased (as in Line B), only the "begin" value and "end" value of the pulse amplitude need be entered by the user, and the "begin" value and "end" value of pulse width will be automatically populated in accordance with a predefined curve.

Alternatively, the user may manually adjust the amplitude value and/or pulse width value when the system 10 is in the SCS mode. In this case, the pulse amplitude value can be manually increased or the pulse width value can be manually decreased via operation of the controls 164, 168 (e.g., such that the pulse amplitude values or pulse width values follow one of Lines A and C illustrated in FIG. 4), or alternatively, the pulse amplitude value can be manually increased via operation of the control 168 and the pulse width value automatically increased (e.g., such that the pulse amplitude values and pulse width values follow Line B illustrated in FIG. 4).

When the system 10 is in the PS mode by clicking the Auto Adjust check box in the auto-adjust control 174, the user may click the start button 158, so that the pulse amplitude value is automatically increased, and the pulse width value is automatically decreased to slowly increase the intensity of the resulting electrical energy (e.g., such that the pulse amplitude values and pulse width values follow Line D illustrated in FIG. 5). In this case, the "begin" value of pulse amplitude need only be entered by the user, and the "end" value of the pulse amplitude and the "begin" and "end" values of the pulse width will be automatically populated, or the "begin" value of the pulse width need only be entered by the user, and the "end" value of the pulse width and the "begin" and "end" values of the pulse amplitude will be automatically populated.

Alternatively, the user may manually adjust the amplitude value or the pulse width value when the system 10 is in the PS mode. In this case, the pulse amplitude value can be manually increased via operation of the control 168 and the pulse width value automatically decreased, or the pulse width value can be manually decreased via operation of the control 164 and the pulse amplitude value automatically increased (e.g., such that the pulse amplitude values and pulse width values follow Line D illustrated in FIG. 5).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of stimulating nerve tissue, comprising:
   applying an electrical stimulus to at least one electrode adjacent the nerve tissue of a patient, the applied electrical stimulus comprising a plurality of pulses defined by a pulse width value and an amplitude value;
   increasing the pulse amplitude value or decreasing the pulse width value; and
   automatically decreasing the pulse width value in response to increasing the pulse amplitude value or automatically increasing the pulse amplitude value in response to decreasing the pulse width value in a manner that increases the intensity of the applied electrical stimulus.

2. The method of claim 1, wherein the pulse amplitude value is increased, and the pulse width value is automatically decreased in response to increasing the pulse amplitude value.

3. The method of claim 1, wherein the pulse width is decreased, and the pulse amplitude value is automatically increased in response to decreasing the pulse width value is decreased.

4. The method of claim 1, wherein the nerve tissue is peripheral nerve tissue.

5. The method of claim 1, wherein the pulse width value is automatically decreased in response to increasing the pulse amplitude value or the pulse amplitude value is automatically increased in response to decreasing the pulse width value in a manner that prevents stimulation of Adelta nerve fibers adjacent the at least one electrode.

6. The method of claim 1, wherein the pulse width value is automatically decreased or the pulse amplitude value is automatically increased in a manner that stimulates nerve fibers of a smaller diameter.

7. The method of claim 1, wherein the electrical stimulus is applied by an implanted pulse generating device, and the pulse amplitude value and pulse width value are adjusted by an external control device.

8. The method of claim 1, wherein the pulse amplitude value is increased manually or the pulse width is decreased manually.

9. The method of claim 1, further comprising implanting the at least one electrode within the patient in contact with the tissue.

10. The method of claim 1, wherein the electrical stimulus is applied to the at least one electrode during a fitting procedure.

\* \* \* \* \*